United States Patent [19]
Greene

[11] 3,970,073

[45] July 20, 1976

[54] POSITIONING DEVICE FOR RADIATION TREATMENT OF CERVICAL CARCINOMA

[75] Inventor: Franklin R. Greene, Flushing, N.Y.

[73] Assignee: Howlin Enterprises, Inc., Old Westbury, N.Y.

[22] Filed: Jan. 30, 1975

[21] Appl. No.: 545,694

[52] U.S. Cl. .................................. 128/1.2; 128/344
[51] Int. Cl.² ........................................ A61N 5/00
[58] Field of Search ............ 128/1.2, 1.1, 303, 361; 128/145.7, 344

[56] References Cited
UNITED STATES PATENTS

| | | | |
|---|---|---|---|
| 3,060,924 | 10/1962 | Rush | 128/1.2 |
| 3,216,413 | 11/1965 | Mota | 128/145.7 |
| 3,323,511 | 6/1967 | Holter | 128/1.2 |
| 3,500,819 | 3/1970 | Silverman | 128/1.2 |
| 3,807,386 | 4/1974 | Rocoplan | 128/1.2 |
| 3,872,856 | 3/1975 | Clayton | 128/1.2 |

*Primary Examiner*—Kyle L. Howell
*Attorney, Agent, or Firm*—McAulay, Fields, Fisher & Goldstein

[57] ABSTRACT

A collapsible, toroidal shaped chamber having top and bottom outwardly extending flanges and an inlet tube to permit collapsing the toroid and filling the toroid. Ovoids containing radioactive material and held in place by tubes which extend down from the ovoids and which tubes extend through opposed openings in the flanges. The toroid is collapsed for insertion and filling with radiopaque material to permit positioning of the ovoids.

4 Claims, 3 Drawing Figures

POSITIONING DEVICE FOR RADIATION TREATMENT OF CERVICAL CARCINOMA

BACKGROUND OF THE INVENTION

My invention is to an improved positioning device for the radioactive treatment of cervical cancer. It is known to apply radiation from, for example, a radioactive caesium source to the malignant tumors. The application of the caesium source is through the positioning of the caesium in an ovoid of a plastic material. The ovoids serve to make sure that the caesium source does not get too close to tissues and thus the ovoid aids in avoiding burning or damaging the tissue. These ovoids essentially perform the function of properly spacing the radioactive source from the tissues to be radiated.

However, positioning the ovoids and holding them in position has posed certain problems. Essentially, the problem is that the mechanism for holding the ovoids has to be inserted into the patient together with the ovoids. As a consequence, the positioning mechanism has to be flexible and adaptable to be inserted into the patient and yet have characteristics which will permit it to hold the ovoids in position during the treatment.

Since the treatment period may run for approximately 48 hours, the positioning mechanism has to hold the ovoids in a desired location while the patient is mobile.

Accordingly, it is a major purpose of this invention to provide a positioning mechanism for the radioactive containing ovoids that are employed in the radioactive treatment of cervical cancer.

It is a related purpose of this invention to provide such a positioning device as can readily be inserted into the patient, can hold the ovoids in position for a period of time while the patient is mobile and is sufficiently conformable so that the patient does not react adversely to the positioning device.

It is a further purpose of this invention to provide a positioning device that will permit checking the position of the ovoids before the radioactive caesium tipped rods are inserted up into the ovoids.

BRIEF DESCRIPTION OF THE INVENTION

In brief, the positioning device of this invention is a collapsible, toroidal shaped chamber having top and bottom outwardly extending flanges and an inlet tube to permit collapsing the toroid and filling the toroid. The flanges have opposed openings through which the tubes supporting the ovoids can be inserted so that the ovoids will ultimately be held in position by the positioning of the collapsible, fillable toroidal positioning device.

In use, the ovoids and the positioning device of this invention are assembled outside of the patient by inserting the stems of the ovoids through the opposed openings of the top and bottom outwardly extended flange of the toroidal chamber. The toroidal chamber is empty and thus collapsible. The chamber is squeezed into a collapsed position so that the assembly can be inserted into the patient. Once inserted and initially positioned in the patient, a radiopaque liquid is flowed through the inlet tube into the toroidal chamber to fill up the toroidal chamber and expand it to its full size and shape. A fluoroscope picture can then be taken to make sure that the ovoids are properly positioned. After proper adjustments are made, the positioning device of this invention properly placed and the ovoids held in the desired position, then, and only then, are the caesium tipped rods inserted through the tubular stems leading to the ovoids and the treatment commenced. In this fashion, radioactivity is applied only from a properly positioned ovoid.

BRIEF DESCRIPTION OF THE DRAWINGS

FIG. 3 shows the caesium tipped rods inserted while FIG. 1 is of the device prior to insertion of the rods.

DESCRIPTION OF THE PREFERRED EMBODIMENT

Figures 1, 2, 3:
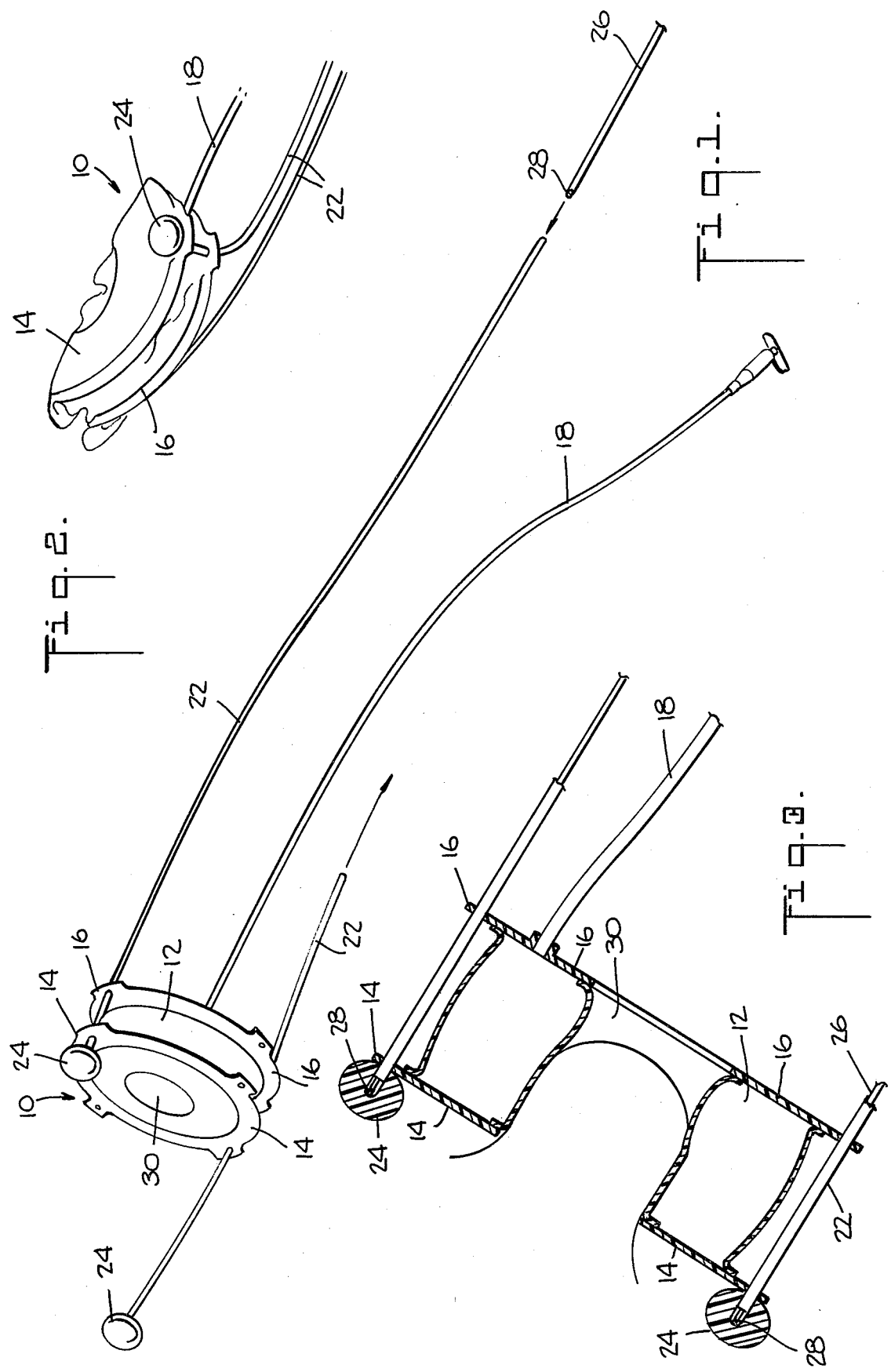
FIG. 1 is a perspective view of an embodiment of this invention showing the positioning device together with two ovoids supported by the device.
FIG. 2 is a pespective view showing the FIG. 1 device collapsed and folded over to facilitate insertion.
FIG. 3 is a longitudinal sectional view through the device of FIG. 1. However

As shown in the FIGS., the positioning device 10 of this invention is essentially a toroidal chamber 12 having outwardly extending upper flange 14 and lower flange 16. These two flanges 14 and 16 are essentially alike. An inlet tube 18 permits access to the interior of the chamber 12. Opposed holes in the flanges 14 and 16 permit tubular stems 22 to which the ovoids 24 are attached to be inserted therethrough.

The walls of the toroidal chamber 12 as well as the flanges 14 and 16 are made of a fairly thin (about 8 mil) vinyl material so that this positioning device 10 can be collapsed or squeezed to a fairly small volume. It can also be shaped as well as collapsed so that insertion into the patient is made convenient. FIG. 2 illustrates the device 10 deflated and folded to permit easier insertion into the patient.

As is known in the art, the support stems 22 for the ovoids 24 are tubular so that the ovoids 24 can be properly and accurately positioned without carrying the caesium radioactive material. Once the ovoids 24 are properly positioned, then and only then, need a caesium tipped rod 25 be inserted up the hollow stem 22 so that the caesium tip 28 is placed in the center of the ovoids 24. Although this technique of after-loading the ovoids 24 has been known, its successful and convenient use and application required a positioning device for the ovoids which is provided by this invention. Having the stems 22 of the ovoids 24 extend through the chamber 12 was tried out and found unsatisfactory because it required too many openings in the chamber 12 walls and thus made retention of the radio-opaque liquid difficult to achieve.

The device 10 is used by inserting the stems 22 through the flange 14, 16 holes (as shown in FIG. 1) and then folding the device (as shown in FIG. 2) for insertion. Upon insertion, the toroidal chamber 12 is evacuated through the inlet 18 and the radio-opaque liquid flowed through the inlet 18 to fill the toroid 12. Once filled, a fluoroscope is used to obtain positioning. Then the caesium tipped rods 26 are inserted.

The central opening 30 in the positioning device 10 has a dual advantage. It permits positioning in the cervix and it permits direct treatment of the cervix.

What I claim is:

1. Apparatus for radio-active treatment of cervical tumors comprising:
    a flexible, collapsible, cylindrical toroidal chamber having an aperture therethrough adapted to be positioned around the cervix, said toroidal chamber having top and bottom surfaces, top and bottom flanges extending radially outward respectively, from said top and bottom surfaces of said chamber, each of said flanges having a plurality of openings, each opening in said top flange being aligned with a corresponding opening in said bottom flange, an inlet tube in communication with the interior of said toroidal chamber and adapted to extend to the outside of the body and to permit flow of radio-opaque fluid into and out of said toroidal chamber, flow of fluid into said chamber when said chamber is collapsed causing said chamber to expand and flow of fluid out of said chamber when said chamber is expanded permitting collapse of said chamber, each pair of aligned openings of said flanges being adapted, when said toroidal chamber is filled, to hold a support stem of an ovoid and to position said ovoid relative to the cervix.

2. The invention of claim 1 further comprising:

a plurality of ovoids, each ovoid having a support stem, each of said support stems extending through a separate pair of said aligned openings.

3. The invention of claim 2 wherein said inlet tube provides the sole means of communication between the interior of said toroidal chamber and the outside.

4. The invention of claim 1 wherein said inlet tube provides the sole means of communication between the interior of said toroidal chamber and the outside.

* * * * *